United States Patent
Van Dyke et al.

(10) Patent No.: US 6,316,598 B1
(45) Date of Patent: Nov. 13, 2001

(54) WATER ABSORBENT KERATIN AND GEL FORMED THEREFROM

(75) Inventors: Mark E. Van Dyke, Fair Oaks Ranch; Cheryl R. Blanchard; Scott F. Timmons, both of San Antonio; Arlene J. Siller-Jackson, Helotes, all of TX (US); Robert A. Smith, Jackson, MI (US)

(73) Assignee: Keraplast Technologies, Ltd., San Antonio, TX (US)

( * ) Notice: Subject to any disclaimer, the term of this patent is extended or adjusted under 35 U.S.C. 154(b) by 0 days.

(21) Appl. No.: 09/394,782

(22) Filed: Sep. 13, 1999

(51) Int. Cl.$^7$ .............. C09H 1/00; C07K 1/00; C08H 1/00; A23J 1/00; A61K 38/16
(52) U.S. Cl. .......... 530/357; 530/355; 530/842; 530/418; 530/422; 530/423; 514/12
(58) Field of Search ................... 424/443, 449, 424/402; 530/357

(56) References Cited

U.S. PATENT DOCUMENTS

| | | | |
|---|---|---|---|
| 4,135,942 | * 1/1979 | Kikkawa | 106/155 |
| 4,357,274 | 11/1982 | Werner | 260/123 |
| 4,369,037 | 1/1983 | Matsunaga et al. | 8/127 |
| 4,439,417 | 3/1984 | Matsunaga et al. | 424/70 |
| 4,495,173 | * 1/1985 | Matsunaga et al. | 424/70 |
| 4,570,629 | 2/1986 | Widra | 128/156 |
| 4,751,074 | 6/1988 | Matsunaga et al. | 424/70 |
| 4,839,168 | 6/1989 | Abe et al. | 424/74 |
| 4,895,722 | 1/1990 | Abe et al. | 424/71 |
| 4,959,213 | 9/1990 | Brod et al. | 514/21 |
| 5,047,249 | * 9/1991 | Rothman et al. | 424/543 |
| 5,134,031 | 7/1992 | Kagechi et al. | 428/373 |
| 5,258,043 | 11/1993 | Stone | 623/66 |
| 5,276,138 | * 1/1994 | Yamada et al. | 530/357 |
| 5,358,935 | 10/1994 | Smith et al. | 514/21 |
| 5,712,252 | 1/1998 | Smith | 514/21 |
| 5,763,583 | * 6/1998 | Arai et al. | 530/353 |
| 5,792,090 | 8/1998 | Ladin | 602/48 |
| 5,824,331 | 10/1998 | Usala | 424/424 |
| 5,932,552 | 9/1999 | Timmons et al. | 424/443 |
| 5,948,432 | * 9/1999 | Timmons et al. | 424/443 |

FOREIGN PATENT DOCUMENTS

| | | |
|---|---|---|
| 0 464 600 A | 10/1991 | (EP) . |
| 56129035 | 10/1981 | (JP) . |
| 5285374 | 11/1993 | (JP) . |
| 5285375 | 11/1993 | (JP) . |
| 6116300 | 4/1994 | (JP) . |
| 6293631 | 10/1994 | (JP) . |
| 6336499 | 12/1994 | (JP) . |

OTHER PUBLICATIONS

Southwest Research Institute Annual Report, 17–18, 21, 1997.
Technology Today, 16(3):9, 1995.
Yamauchi, et al., "Cultivation of fibroblast cells on keratin-coated substrata," Polymers of Tissue Engineering, 329–40, 1998.
Blanchard, et al., U.S. application Serial No. 09/057,161.
Timmons, et al., U.S. application Serial No. 09/198,998.
Van Dyke, et al., U.S. application Serial No. 09/330,550.

* cited by examiner

Primary Examiner—Thurman K. Page
Assistant Examiner—Isis Ghali
(74) Attorney, Agent, or Firm—Timothy S. Corder; Stephen J. Moloney; Vinson & Elkins L.L.P.

(57) ABSTRACT

A hydratable, highly absorbent keratin solid fiber or powder capable of absorbing a large weight excess of water may be produced by partially oxidizing hair keratin disulfide bonds to sulfonic acid residues and reacting the sulfonic acid residues with a cation. The neutralized suspension can be filtered, washed, and dried, leaving keratin solid which can be shredded into fibers and further ground into powder. Addition of water to the solid produces a hydrogel. The powder or hydrogel may be useful as an absorbent material, as a therapeutic for skin, or as an excipient. Another use for the hydrogel is as a biocompatible viscoelastic filler for implant applications.

53 Claims, No Drawings

WATER ABSORBENT KERATIN AND GEL FORMED THEREFROM

RELATED APPLICATIONS

The present application is related to concurrently filed U.S. patent application entitled Implantable Prosthetic Device, with the same inventors as the present application.

FIELD OF THE INVENTION

The present invention is related generally to a keratin composition and method for making same. More specifically, the present invention relates to an absorbent keratin powder or fiber. In particular, the present invention includes a hydratable keratin solid which forms a hydrogel upon addition of water for use in various applications including diapers, skin treatments, prosthetic devices, excipients, and the like.

BACKGROUND OF THE INVENTION

Absorbent materials are currently used to absorb body fluids such as urine, menses, and wound exudate. The absorbent materials are placed near the skin to serve this purpose. One class of products includes diapers, where the absorbent material can be derived from wood pulp, cellulosic fibers, or super absorbent, synthetically produced material. Diapers commonly have an inner core designed to absorb urine and water. The core is typically formed from a superabsorbent polymer dispersed in a larger amount of less absorbent material. The absorbent materials typically contained in the core are separated from the skin by at least one layer of material. The absorbent materials absorb urine and can become saturated. It is believed that some material from the absorbent core leaches from the wet absorbent and travels back to the skin. In the case of chemically treated absorbent materials and films, depending on the chemicals, the leachate may be irritating and is not believed to be beneficial. Skin contact with urine can also occur and result in irritation. This type of irritation may exacerbate diaper rash problems.

Other products which contain absorbent materials for use next to the skin include feminine hygiene products such as tampons and pads. These products serve to absorb menses. Another class of products using absorbent materials includes wound dressings, both those designed for humans, and dressings for veterinary use for application to wounds or skin irritations or disorders in animals. For specific applications, wound dressings preferably absorb exudate from wounds while keeping the wounds relatively moist to promote healing. In some applications, a gel may be desirable as a wound dressing, where the gel can maintain a moist wound environment, while absorbing excess exudate.

What would be desirable is an absorbent material formed from a natural product. What would be beneficial is a non-toxic, non-antigenic product derived from natural sources that would cause no concern when leachate from the material contacts the body or the material itself contacts the body. What would be advantageous is a material that can absorb urine and, when wet, leach out a natural product that is beneficial with respect to diaper rash. What would be desirable is a material that can return a skin healing leachate to the skin. What would be desirable is a material that aids wound healing. What would be desirable is a hydrogel made of natural products formable by adding water to a powder or fiber.

SUMMARY OF THE INVENTION

The present disclosure addresses at least some of the deficiencies in the art by providing a hydratable, hydrogel-forming solid derived from a keratinous source such as hair, fur, human hair and the like. In certain embodiments, a hydrogel-forming solid as disclosed herein may absorb up to 5 to 20 times its weight in water to form a hydrogel. Such a solid, as well as the hydrogel formed from the solid will be useful in various applications such as use as an absorbent with skin healing properties when incorporated into diapers, feminine hygiene products, wound dressings, including both human and veterinary uses, as a soft tissue augmentation medium when used in subdermal implants, as a moisture containing agent in cosmetics, oils, lotions, or gels for use on the skin, in applications related to the healing of damaged skin, and as a pharmaceutical excipient for sustained release pharmaceutical applications.

A hydratable keratin solid may be made by methods that include providing a keratinous material, or keratin, having disulfide linkages and partially or substantially oxidizing the keratinous material with an oxidizing agent, for example, such that some disulfide linkages are cleaved and oxidized, forming hydrophilic sulfonic acid or cysteic acid residues. A preferred source of keratinous material is human hair, although the keratin may be obtained from hair or fur of animals including any mammal, or from finger or toenail material or from hooves, feet, beaks, skin, feather or horns. Human hair is a preferred source of keratin because of its ready availability from cuttings of barber and beauty shops, because it is expected to be less prone to cause undesirable immune or allergic reactions in a human, and because a keratin preparation may be made from the hair of a subject for whom the preparation will be used. This last advantage can be especially important in embodiments involving subdermal implantations.

It is well known in the art that keratins contain substantial sulfur, that is, the amino acid sequence of keratin contains a high proportion of cysteine residues as compared to proteins in general. These cysteines each include a sulfhydryl moiety that is able to bond with another sulfhydryl moiety from another cysteine residue to form a disulfide bond. The second cysteine may reside within the same keratin molecule, or in another keratin molecule. These disulfide bonds are responsible for much of the tertiary and/or quaternary structure of this class of proteins. A suitable oxidizing agent is able to break this disulfide bond and to oxidize one or both of the sulfhydryl moieties so that they are no longer able to form a disulfide. Such an oxidation is a part of the process of forming the keratin products of the present disclosure. Preferred oxidizing agents include, but are not limited to peracetic acid, hydrogen peroxide, perborates, percarbonates, benzoyl peroxide, or ammonium sulfate peroxide. However, any suitable oxidizing agent known in the art can be used in the practice of the invention. After oxidation, the liquid oxidizing agent can be filtered from the oxidized keratin solid, and the solid may be washed to remove residual oxidizing agent, for example.

The resulting solid may then be suspended in a non-aqueous solvent and the pH may be adjusted upward with base—conveniently to at least neutral pH. Preferred solvents for this second solution do not include significant water as the water may hydrolyze the peptide backbone during processing. Preferred solvents would include alcohols such as methanol, ethanol, or propanol, for example, and would also include non-aqueous polar, water-miscible solvents such as acetone and tetrahydrofuran, for example. An effective solvent should be able to solvate a Lewis base and should also be able to provide a medium able to keep the keratin sufficiently open to allow ionic associations or interactions between the base cations and anionic sulfonic acid groups in the keratin. Preferred bases include, but are not limited to sodium hydroxide, potassium hydroxide and ammonium hydroxide, which, as is known in the art, would yield or produce sodium, potassium and ammonium cations, respectively, upon entering solution.

The keratin suspension may be heated, and is preferably heated to boiling for a time sufficient to swell the keratin. The keratin suspension may be stirred without heat for a longer period of time to allow a more complete association or reaction between the sulfonic acid groups and the base cations. The continued reaction time at or near room temperature, or even below room temperature while stirring is contemplated by the inventors to allow the base cations to approach and bind to the keratin anionic sites with a lower incidence of peptide backbone degradation that could occur with continued boiling. The cations for use in the present invention, therefore, must be able to interact with the anionic cysteic groups in the keratin material. The use of the term "cations" or "monovalent cations" in the present disclosure and claims is indication of those cations that are able to do so. After a sufficient reaction time, the keratin solid may be removed from the suspension by filtration, for example, and dried, leaving a solid salt formed of the keratin sulfonic acid or cysteic acid groups and base cations. This solid may be shredded into a fibrous form and/or ground into a finely divided powder. This solid may be used in certain embodiments, or it may be hydrated by adding water, for example, and the hydrogel, or viscoelastic hydrogel thus formed may be used in certain embodiments.

In certain embodiments, an absorbent keratin layer may be incorporated into various absorbent articles such as a disposable diaper, a wound dressing, or feminine hygiene product, by adsorbing or coating a keratin solid or hydrogel onto a layer of the article, by impregnating a component of such an article, or by associating a keratin material with a non-woven layer of such an article. In certain embodiments an absorbent keratin powder may be applied directly to skin to absorb moisture and inhibit rashes or chafing, such as diaper rash, for example. A hydratable keratin solid of the invention may have an absorbency of 1, 5, 10, 15 or even up to 20 times its weight in water. The absorbency may be adjusted by, for example, varying the degree of oxidation of the keratin in the process. It may thus provide a substitute for products such as talc and cornstarch. The inventors have demonstrated, for example, that a fibrous or powdered form of solid keratin material as described herein can absorb about 10 times its weight in water in about 10 seconds.

The hydratable keratin solids as described herein form a hydrogel or a viscoelastic hydrogel upon application of water, and also are contemplated to contain skin healing peptides associated with the keratin, which may leach out of the keratin products when wet. The keratin products thus provide an added benefit, in addition to water absorbency, that is, healing or soothing peptides are also released that may have beneficial effects on the skin of a user of the products. This property offers certain benefits in embodiments such as wound dressings, as well as cosmetics, gels or lotions for application to the skin.

In certain embodiments a keratin absorbent as disclosed herein may be used as a wound dressing material to absorb wound exudate by direct application, or by incorporation into a dressing. The solid, hydratable forms of keratin offer certain advantages in such applications because they may be stored as dry powders or fibers and hydrated to form a gel in the field, or only as needed, for example. Medical applications, such as wound exudate management or drug release, can make use of the keratin material in absorbent powder, fiber, woven fiber, or felt form.

The keratin hydrogel is also believed to be suitable for use as an implant filler, for example, used to fill a breast implant, or to augment soft tissue for cosmetic, reconstructive or aesthetic reasons, or in a tissue expander application. The keratin product may also be used in cosmetics to retain moisture next to the skin. The performance of cosmetics which reduce the greasy appearance of skin can be enhanced through the use of moisture absorbent keratin material as an additive or base ingredient, for example, in a cosmetic formulation. The keratin absorbent and hydrogel can also be used for a variety of tissue engineering applications. Both materials may act as biocompatible scaffolds that provide a mitogen, the keratin peptide, to the cellular components of a tissue-engineered implant.

The present invention may be described, therefore, in certain aspects as a composition comprising a hydratable keratin solid, wherein the solid comprises a keratin where at least a portion of the cysteic groups of the keratin are jonically or electrostatically associated with, or may be ionically bound to cations. As used herein, ionically bound or ionically associated would have their ordinary meaning as is known in the art, and would include the electrostatic attraction between an anion and a cation, and would include such interactions directly, such as through formation of ionic bonds, and interactions through intermediary bipolar moieties, for example. A cysteic group would include cysteine and derivatives of cysteine including cysteine and cysteic acid or sulfonic acid. As used herein, cysteic acid and sulfonic acid denote a cysteine side chain in which the terminal sulfur is bonded to three oxygen atoms to produce the sulfonic acid ion, $SO_3^-$, or the acidic form, $SO_3H$. In certain embodiments, a portion of the cysteic groups are oxidized to sulfonic acid or cysteic acid groups. Sulfonic acid or cysteic acid groups may comprise a significant portion of the total cysteic groups and in some embodiments the sulfonic acid groups may constitute a major portion of the total cysteic groups. The extent of the oxidation may be adjusted by adjusting certain parameters of the oxidation reactions, such as temperature, concentration of oxidizing agent, and time of reaction, for example, to achieve a product with certain desired properties, such as absorbency or resiliency, for example.

In certain embodiments, therefore, the present invention may be described as a hydratable keratin solid made by a process comprising oxidizing a portion of the cysteic acid groups of a keratin to obtain a keratin having oxidized cysteic groups, and contacting the keratin having oxidized cysteic groups with monovalent cations under conditions effective to form ionic associations or ionic bonds between at least a portion of the oxidized cysteic groups and the cations.

In some embodiments, the hydratable keratin solid is made by a process comprising oxidizing at least a portion of the cysteic acid groups of a keratin to obtain a keratin having oxidized cysteic groups, and contacting said keratin having oxidized cysteic groups with monovalent cations under conditions effective to form ionic associations or ionic bonds between a substantial portion of said oxidized cysteic groups and said cations. The oxidation may comprise placing the keratin in a solution containing a concentration of an oxidizing agent effective to oxidize a portion of the cysteic acid groups. The portion of oxidized cysteic groups may be a major portion of the total cysteic acid groups.

In certain embodiments of the present invention, the oxidation comprises placing the keratin in a solution containing a concentration of hydrogen peroxide, peracetic acid, perborates, percarbonates, benzoyl peroxide or ammonium sulfate peroxide effective to oxidize a portion of the cysteic groups.

The process of the present invention may further comprise heating the keratin solid containing oxidized cysteic groups in a solvent solution containing a dissolved base, wherein the base produces the monovalent cations in the solution. The solvent solution may comprise a solvent selected from methanol, ethanol, propanol, ether, tetrahydrofuran (THF), acetone, propylene glycol, 1,4-dioxane, and glycol ether. In certain embodiments the process further comprises removing the solution from the heat and stirring for a time effective to form ionic bonds between the cysteic groups and cations produced by the base. The process may also further comprise drying the keratin solid, such as by drying a solid or solution under vacuum.

Another aspect of the present invention is a composition comprising a keratin hydrogel wherein the hydrogel is produced by adding water to a composition comprising a hydratable keratin solid, wherein the solid comprises a keratin where at least a portion of the cysteic groups of the keratin are ionically bound to cations. In some embodiments, the composition of the present invention comprises a keratin viscoelastic hydrogel produced by adding water to a composition comprising a hydratable keratin solid, wherein the solid comprises a keratin where a portion of the cysteic groups of the keratin are ionically bound to or associated with cations.

Another aspect of the present invention is a process for making a hydratable keratin solid comprising: (1) oxidizing keratin in a first solution comprising a soluble oxidizing agent, such that a portion of the disulfide bonds of the keratin are oxidized to form sulfonic acid residues, to obtain an oxidized solid fraction; (2) separating the oxidized solid fraction from the first solution; (3) contacting the oxidized solid fraction with a second, basic solution comprising a monovalent cation dissolved in a solvent; (4) maintaining the second solution containing the oxidized solid fraction and the monovalent cations for a time and at a temperature effective to allow an interaction between the sulfonic acid residues and the monovalent cations to obtain a salt solution of the keratin and the monovalent cation; and (5) substantially removing the solvent from the salt solution to obtain a pure hydratable keratin solid.

The process may also further comprise adjusting the pH of the second solution, to obtain a substantially neutral solution. In some embodiments, the keratin is obtained from hair, fur, skin, feet, beaks, horns, hooves or feathers and is preferably obtained from human hair.

In some embodiments, the keratin is oxidized by suspending the keratin in a solution of a suitable oxidizing agent such as one selected from the group consisting of hydrogen peroxide, peracetic acid, perborates, percarbonates, benzoyl peroxide, and ammonium sulfate peroxide, in a concentration of between about 1 and about 35 weight/volume percent. In various embodiments, the keratin is oxidized by suspending the keratin in a solution of an oxidizing agent selected from the group consisting of hydrogen peroxide, peracetic acid, perborates, percarbonates, benzoyl peroxide, and ammonium sulfate peroxide, in a concentration of about 1, or about 2, or about 3, or about 4, or about 10, or about 15, or about 20, or about 30, or about 32, or about 35 weight/volume percent. As used herein the term weight/volume percent refers to a solution in which the concentration is determined in weight percent, that is then diluted into a particular volume, arriving at a weight/volume percent. For example, in order to arrive at the oxidant solutions described herein a "stock solution" at fairly high concentration is diluted in water. As an example, hydrogen peroxide may be purchased as a 30 weight % solution (30 grams of peroxide per 100 grams of solution). To make 1 liter of a 2% solution of this, one would dilute 66.7 mL of the 30 weight % stock solution in 933.7 mL of water. The net effect is to cut the stock solution 15-fold (from 30 down to 2%). This ratio is a weight to volume ratio, so the resulting solution is described as 2 weight/volume %.

In some embodiments, the keratin is oxidized by suspending the keratin in a solution of a suitable oxidizing agent, such as one selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. In other embodiments the temperature is between about 4° C. and about 90° C., or between about 20° C. and about 100° C., or between about 90° C. and about 100° C. In other embodiments, the temperature is about 4° C., or about 90° C., or about 100° C.

The present invention may also include the process wherein the keratin is oxidized by suspending said keratin in a solution of an oxidizing agent selected from the group consisting of hydrogen peroxide, peracetic acid, perborates, percarbonates, benzoyl peroxide, and ammonium sulfate peroxide, in a concentration of between about 1 and about 35 weight/volume percent, at a temperature between about 0° C. and about 100° C. for a period of between 0.5 and about 24 hours, or in a concentration of oxidizing agent of between about 1 and about 35 weight/volume percent, at a temperature between about 0° C. and about 100° C. for a period of between 1 and about 2 hours, or for between about 2 and about 4 hours, or for between about 1 and about 4 hours, or for a period of about 10 hours.

More specifically, the present invention may include oxidizing the keratin by suspending the keratin in a solution of between about 1 percent to about 32 percent peracetic acid at a temperature between about 0° C. and about 100° C. for between about 0.5 and about 24 hours, or by suspending the keratin in a solution of about 1 percent peracetic acid at a temperature between about 0° C. and about 100° C. for between about 0.5 and about 24 hours, or by suspending the keratin in a solution of between about 4 percent peracetic acid at a temperature of about 4° C. for 24 hours, or by suspending the keratin in a solution of about 4 percent peracetic acid at room temperature for about 24 hours, or by suspending the keratin in a solution of about 4 percent peracetic acid at about 90° C. for about 10 hours, or by suspending the keratin in a solution of about 4 percent peracetic acid at a temperature between about 20° C. and about 100° C. for between about 1 and 4 hours, or by suspending the keratin in a solution of about 4 percent peracetic acid at a temperature between about 80° C. and about 100° C. for between about 1 and about 2 hours, or even by suspending the keratin in a solution of about 2 percent peracetic acid at a temperature between about 0° C. and about 100° C. for about 2 hours.

A second solution in the process of making the disclosed compositions, wherein the second solution contains the oxidized solid fraction and monovalent cations may be heated, and may also be boiled for between about 0.5 hours and about 12 hours, for between about 0.5 hours and about 3 hours, or for about 1 hour. When said solution is boiled, the solution may be allowed to continue reacting while being stirred after removal of the heat. Alternatively, the solution may be stirred and allowed to react without the application of heat, or of boiling temperatures. In certain embodiments, the solution is allowed to react at a temperature of between about 15° C. and about 30° C. for a period of between about 1 and about 24 hours, or at a temperature of between about 20° C. and about 25° C. for a period of between about 1 and about 5 hours, or at room temperature for a period of about 5 hours. In certain preferred embodiments the solution is heated to the boiling point of the solvent and boiled for 2 hours.

Certain processes as described herein are effective to produce a hydratable keratin solid, and it is an embodiment of the present invention that those solids may be hydrated by the addition of water to obtain keratin hydrogels, or even viscoelastic keratin hydrogels. The terms hydrogel and viscoelastic hydrogel, as used herein, are meant to have the art recognized definition, and could be described as absorbing water such that the water cannot be removed by mechanical methods such as pressure or centrifugation. Viscoelastic hydrogels would also be defined as gels that display non-Newtonian fluid properties.

In certain embodiments the present invention may be described as a disposable diaper that includes a hydratable keratin solid, or a diaper which incorporates a hydratable or absorbent keratin solid. A hydratable keratin solid may be coated on a layer of the diaper, either a layer next to the skin of a wearer, or a layer separated from the skin of a wearer by a water permeable layer. In certain embodiments a hydratable keratin solid may be associated with a non-woven layer of a diaper, or may be impregnated into a layer of a disposable diaper, or it may be contained in an inner absorbent core.

In certain alternative embodiments, the present invention may be described as a feminine hygiene product, or a wound dressing that includes a hydratable keratin solid. As was described for use in diapers, a hydratable keratin may be coated on a layer of a product, associated with a non-woven layer of a product, or even impregnated into a layer of a product or contained in an absorbent core. Exemplary products would include wound dressings, tampons, and sanitary pads.

Certain embodiments of the invention may be described as methods for promoting healing of skin in a subject including a human or an animal having damaged skin, including providing an absorbent, keratin material, wherein a portion and preferably a substantial or major portion of the cysteic groups of said keratin are oxidized and wherein water soluble peptides are associated with the keratin, wherein at least some of said peptides can leach out from said keratin upon application of water, and wherein said peptides promote healing of damaged skin; and disposing the absorbent keratin material near damaged skin, such that moisture causes at least some of said peptides to leach out of said keratin and to contact said skin. The method may be practiced with animal or human subjects, such that either animal or human skin is healed by this method. The practice of the method for promoting skin healing as described herein may include the treatment of damaged skin including, but not limited to diaper rash, burn, sunburn, cut, abrasion, puncture, a sore, bed sore, ulcer, diabetic ulcer, irritated skin, surgical incision, skin graft donor site, or wrinkled skin. It is understood that in the practice of such embodiments, the wound of the subject being treated may exude or excrete moisture and that the absorption of such moisture by said keratin may cause the release of water soluble peptides from keratin products of the present invention.

In certain embodiments the present invention may be described as a method for promoting skin healing, in particular in those embodiments in which a keratin solid or hydrogel as described herein, such as a keratin solid or hydrogel in which the keratin is obtained from human hair, for example, is contained in, or forms a portion of a cream, lotion, or gel for application to skin, hair, lips, or nails, for example. Such formulations can offer various advantages such as moisturizing the skin, or inhibiting loss of moisture from the skin, as well as providing the healing effects of peptides that may leach from the keratin containing product. Such creams, lotions and gels may be applied to damaged skin, such as dry, burned, sunburned, wrinkled, cut, scraped, chapped, irritated, ulcerated or otherwise damaged skin or other tissue.

Creams, lotions, or gels of the present invention may incorporate or replace other ingredients known in the art, including, but not limited to oleaginous, emulsifiable, emulsion base, or water-soluble ointment bases as are well known in the pharmaceutical arts. Oleaginous bases that may be combined with the keratin compositions include ointments containing white wax and/or white petrolatum, ointments containing yellow wax and petrolatum, cetyl esters wax, oleic acids, and paraffins. Absorbent ointment bases or emulsifiable bases that may be used include those containing anhydrous lanolin, or combinations of cholesterol, stearyl alcohol, white wax and petrolatum, for example. Emulsion bases and components that may be used include ointments containing cetyl alcohol, and cold creams such as those containing cetyl esters wax, white wax, mineral oil, sodium borate and water, for example. Other ointments of the present invention may contain glyceryl monostearate, lanolin, stearic acid, or a combination of methylparaben, propylparaben, sodium lauryl sulfate, propylene glycol, stearyl alcohol and white petrolatum, for example, or an ointment containing cetyl esters wax, white wax, almond oil, sodium borate, stronger rose water, and rose oil, for example. Water soluble ointments and creams for use in the present invention may include glycol ethers and derivatives thereof, polyethylene glycols, polyoxyl 40 stearate, and/or polysorbates.

The preparations as described herein for topical applications may also include protectives and absorbents, demulcents such as benzoin, hydroxypropyl cellulose, hydroxypropyl methylcellulose, polyvinyl alcohol, propylene glycols, sodium alginates, and tragacanth. Emollients, astringents, or antiperspirants may also be included in the keratin containing formulations as described herein.

An aspect of the present disclosure is a method for augmenting soft tissue in a subject comprising injecting a keratin composition as described herein subdermally in an area in need of augmentation. A variety of such applications are available in light of the present disclosure and would include augmentation of soft tissue including, but not limited to augmentation of a urinary sphincter in order to improve elasticity and alleviate urinary incontinence, augmentation of vocal chords to restore elasticity, as well as improvement of the appearance of a subject by augmentation of breasts, lips, chin, gluteal area, or even to improve wrinkled or acne scarred skin, or skin scarred by other conditions, and including soft tissue voids or indentations. A keratin composition may be provided as a dry solid and hydrated after subdermal implantation, or a hydrogel or viscoelastic hydrogel may be prepared and implanted. In certain embodiments, a dry or hydrated keratin material may be contained in a biocompatible envelope, bag, or container for subdermal implantation, and hydrated after implantation by addition of water or absorption of body fluids, or a keratin material may be suspended in an injectable carrier and injected in the desired area of augmentation.

It is an aspect of the present invention that a keratin composition as described herein, and in particular keratin obtained from human hair is also useful as an excipient for the delivery of a pharmaceutical agent, and in particular in the sustained or delayed release of a pharmaceutical agent. An embodiment of the invention may be described, therefore, as a composition comprising a keratin having oxidized cysteic groups and a pharmaceutically active agent. Such a formulation may include a hydratable keratin solid excipient, or a keratin hydrogel depending on the particular application.

In the practice of the invention, a dry hydratable keratin as described herein may be mixed with a powdered pharmaceutical agent and water added to hydrate the mixture, or alternatively such a solid mixture may be formulated as a compressed tablet to be orally administered or for extemporaneous preparations for injection, or as a molded tablet, or it may be enclosed in a capsule for oral administration or subdermal implantation, for example. In certain embodiments a solution containing a water soluble drug or pharmaceutical agent may be added to a hydratable keratin so that the agent is carried into a hydrogel along with the water. A prepared hydrogel, or dry formulation may also be enclosed in a digestible or biodegradable capsule, such as a hard gelatin capsule for oral administration. In certain embodiments, the described pharmaceutical preparations may be formulated for injection, either intravenous, subcutaneous, or intramuscular, for example, or for inhalant, for eye, ear, or nose drops, or for administration as a suppository.

In certain embodiments an active pharmaceutical agent may be associated with a keratin excipient by non-covalent attraction or association, through electrostatic, hydrophobic or ionic interaction, for example, or it may be covalently attached to a keratin excipient by covalent bonding to an oxidized keratin as described herein. In certain embodiments an active agent such as a drug is physically or sterically entrapped within a keratin hydrogel and released over time by diffusion, or as a keratin excipient is degraded.

It is understood that the pills formulated for oral administration, including a hydratable keratin solid, or even pills, capsules or tablets containing a keratin hydrogel may contain ingredients to serve as additional fillers, binders and for color coding purposes. These ingredients are in common use in present pharmaceutical formulations and may include, but are not limited to, lactose, corn starch, calcium phosphate, povidone, magnesium stearate, stearic acid, colloidal silicon dioxide, hydroxypropyl methylcellulose, polyethylene glycol and one or more of the following dyes: FD&C Blue No. 1 Lake, FD&C Blue No. 2 Aluminum Lake, D&C Green No. 5, D&C Yellow No. 10, FD&C Yellow No. 6 or FD&C Red No. 3. Of course these are only exemplary fillers and dyes, those of skill in the art will recognize that other inactive ingredients may be used in the preparation of the formulations of the present invention.

Keratin excipient preparations as described herein may be prepared for oral administration, and would also include injectable solutions or suspensions for intramuscular or subcutaneous implantation including long acting injections, suppositories, topical ointments and transdermal applications such as skin patches. Other ingredients may include a surfactant, such as hydroxypropylcellulose. Dispersions can also be prepared in glycerol, liquid polyethylene glycols, and mixtures thereof and in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. The carrier can be a solvent or dispersion medium containing, for example, water, ethanol, polyol (for example, glycerol, propylene glycol, and liquid polyethylene glycol, and the like), suitable mixtures thereof, and vegetable oils. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride.

Suitable pharmaceutical agents for use with the excipients described herein would include any pharmaceutical agent that can form an association with the keratin formulations through non-covalent, covalent, or steric interaction. Such agents that are particularly suited to oral administration may include antibiotics such as acetaminophen, tetracyclines, penicillins, vitamins, anatacids, non-steroidal antiinflammatory agents, anesthetics, breath fresheners, and minerals, for example.

In those embodiments in which transdermal administration is desired, the disclosed compositions may be formulated to be administered by use of a skin patch, or transdermnal delivery system. Transdermal administration may be accomplished by any of a number of systems known in the art. Examples of systems that may be adapted for use with the compositions described herein include those systems of transdermal administration described in U.S. Pat. No. 4,816,252; U.S. Pat. No. 5,122,382; U.S. Pat. No. 5,198,223; U.S. Pat. No. 5,023,084; U.S. Pat. No. 4,906,169; U.S. Pat. No. 5,145,682; U.S. Pat. No. 4,624,665; U.S. Pat. No. 4,687,481; U.S. Pat. No. 4,834,978; and U.S. Pat. No. 4,810,499 (all incorporated herein by reference.)

These methods typically include an adhesive matrix or drug reservoir system and may include a skin permeation enhancement agent such as ethanol, polyethylene glycol 200 dilaurate, isopropyl myristate, glycerol trioleate, linolenic acid saturated ethanol, glycerol monooleate, glycerol monolaurate, n-decyl alcohol, capric acid, and certain saturated and unsaturated fatty acids, and their esters, alcohols, monoglycerides, acetate, diethanolamides and N,N-dimethylamides (See for examples, U.S. Pat. No. 4,906,169).

The release rate of a keratin excipient preparation is determined by the rate at which water is absorbed and the keratin solid disintegrates. The water absorption rate of the solid keratin can be controlled by the number of sulfonic acid residues generated in the oxidationn procedure. By exposing the keratin source material to extremes of oxidant concentration, temperature, and time, extremes of absorption rate can be obtained. For example, at low oxidant concentration, colder termperatures and short time periods, relatively few disulfide residues will be converted to sulfonic acid residues. Such a keratin solid, further processed as described herein will absorb relatively little water and disintegrate relatively slowly. Conversely, a keratin solid prepared at high oxidant concentration, at boiling temperature for a long time period, further processed as described herein, will absorb relatively large amounts of water and disintegrate relatively quickly. Disintegration rates between these extremes can be obtained by processing the keratin source material using intermediate conditions.

DETAILED DESCRIPTION OF THE INVENTION

The present invention includes a hydratable solid derived from keratin which is highly absorbent and can form a hydrogel or viscoelastic hydrogel upon the application of water. The keratin solid can include protein having an ionizable pendant group such as sulfonic acid which can be derived from an oxidized protein disulfide linkage. A preferred source of protein is keratin, and particularly preferred is keratin obtained from hair, including human hair. While hair is a preferred source of keratinous material, other keratinous materials are also believed suitable for use in the present invention. Examples of other sources include animal hair, skin, hooves, feathers, beaks, feet and horns. The patient or a human donor are some preferred sources of hair, as hair from these sources is most likely to result in a non-antigenic product, although animal hair may be acceptable for many individuals for many applications. In one method according to the present invention, hair is provided, preferably clean and unbleached. In another method, the hair is washed with Versa-Clean ™ (Fisher Scientific, Pittsburgh, Pa.), rinsed with deionized water, and allowed to dry.

The hair can be oxidized in peracetic acid or another suitable reagent such as $H_2O_2$. One method utilizes between about 1% to 32% peracetic acid, at a temperature between about 0 degrees C and 100 degrees C for between 0.5 and 24 hours. In one method, about 1 weight/volume percent peracetic acid is used. One method treats 30 grams of hair with 500 mL of 4% peracetic acid at 4 degrees C for 24 hours. Another method treats the hair at room temperature for 24 hours. Yet another method treats the hair at about 90 degrees C for about 10 hours. In a preferred method, the hair is treated by heating the hair in the oxidizing agent for between about 1 and 4 hours at a temperature between about 20 and 100 degrees C. In a more preferred method, the hair is treated by heating the hair in the oxidizing agent for between about 1 and 2 hours at a temperature between about 80 and 100 degrees C. In a most preferred method, the hair is treated by heating the hair in about 2 weight/volume percent oxidizing agent for about 2 hours at a temperature of about 100 degrees C. The oxidation is believed to cleave a significant portion of keratin disulfide bonds forming cysteic acid residues having sulfonic acid groups. The sulfonic acid groups are believed to be hydrophilic in nature and will ionically bond to cations later in the process, forming a salt of the keratin and cation. The partial oxidation is also believed by Applicants to form short chain peptides, which can remain associated with, or entrained in the keratin structure.

After oxidation, the keratin solid can be recovered from the oxidizing liquid using filtration or other suitable methods such as centrifuigation or decantation. The recovered, oxidized solid can be washed with water or alcohol such as methanol or ethanol to remove the excess oxidizing agent. In a preferred embodiment, washing is limited to avoid removing too much of any soluble peptide chains entrained in the keratin.

The solid fraction can be suspended in a suitable solvent. The solvent should be capable of at least suspending the hair or keratin solid and keeping the solid sufficiently open for subsequent reaction. The solvent is preferably a non-aqueous solvent, as the presence of water can act to hydrolyze peptide backbone bonds, which can result in an inferior product. The solvent should be able to solubilize the later added base. One group of suitable solvents includes alcohols such as methanol and ethanol. Other solvents such as ether, tetrahydrofuran (THF), acetone, propylene glycol, 1,4-dioxane and glycol ethers may also be suitable as solvents. The solvent used is preferably volatile to promote evaporation from the final solid product.

The hair or keratin solvent suspension can then have the pH titrated upward to at least about pH 7. Increasing the pH deprotonates the sulfonic acid groups, leaving the sulfonic acids free to exchange with another cation. The pH can be adjusted with a base, preferably having a monovalent cation. Preferred bases include sodium hydroxide and potassium hydroxide.

The pH-adjusted keratin suspension can be heated for a time and temperature sufficient to open the keratin structure and promote neutralizing of the sulfonic acid sites with the provided cation. In a preferred method, the keratin suspension is boiled between about 0.5 hours and 12 hours. More preferably, the keratin suspension is boiled between about 0.5 hours and 3 hours. In one method, the keratin suspension is boiled for about 1 hour. Boiling for too long a time period is believed to lead to a final, swelled or mushy keratin which may result from degradation of the peptide backbone. A swelled keratin product is less preferred due to the greater difficulty of grinding the keratin.

After boiling, the keratin is preferably allowed to continue to react with the provided base cation at lower temperature and with stirring. The lower temperature reaction preferably takes place at a temperature of between about 15 and 30 degrees C for between about 1 and 24 hours. More preferably, the lower temperature reaction takes place at a temperature of between about 20 and 25 degrees C for between about 1 and 5 hours. In one method, the keratin suspension is allowed to react with stirring at room temperature for about 5 hours. In certain embodiments the reaction is held at the boiling point of the solvent for about 2 hours.

After reacting at lower temperature, the reacted solid can be separated from the solvent using any suitable method such as filtration. The solid is preferably washed with a solvent such as the same solvent used in the reaction. Washing the keratin removes some of the base, which is preferably removed. The base is preferably removed to make the keratin solid less caustic.

After filtration and washing, the keratin can be dried by a method such as evaporation under vacuum. In one method, the keratin is dried at room temperature under about 5 mm Hg vacuum for about 2 hours. The dried keratin is preferably somewhat brittle, which can result in a better product after grinding. The dried keratin can be shredded into fibers and can further be ground into a powder. The dried keratin can be directly ground into a powder using a mortar and pestle, a ball mill, or other means of breaking down or comminuting the dried keratin into particles. Alternatively, the keratin can be ground or milled in the solvent used for said neutralization step.

One resulting hydratable fiber or powder has been observed to absorb about 10 to 13 times its own weight in water. In one test, fibers having a length of between one quarter and one-half inch were observed to absorb an average of 1300% +/−33% of their weight in water at a temperature of 21.5 degrees C. The fiber has been observed to absorb at least 10 times its own weight in water within about 10 seconds. The powder has been observed to rapidly absorb water as well.

One use for the keratin powder and fiber is as a disposable diaper filler material. Disposable diapers typically have an absorbent inner layer which is often filled with a superabsorbent polymer and cellulosic material, often chemically derived from wood pulp. In one application of the keratin material, a layer of the hydratable keratin is positioned in a disposable diaper near the skin but separated from the skin by a permeable layer. The hydratable keratin layer can serve to absorb urine and water from the wearer. In some embodiments, the hydratable keratin includes a substantial fraction of soluble peptides having wound healing properties, as discussed in co-pending U.S. patent application Ser. No. 09/330,550, filed Jun. 11, 1999, entitled SOLUBLE KERATIN PEPTIDE, herein incorporated by reference. The water-soluble peptides are believed to be entrained in the keratin structure and able to leach out when water is applied. In use, the keratin layer remains dry until soaked with urine, at which point the soluble peptides can diffuse out of the keratin. The soluble peptides dissolved in the liquid present can thus come in contact with the skin. The wound healing properties of the peptides are believed to be beneficial in treating diaper rash.

In another use, the hydratable keratin powder or fiber can be used as an ingredient in cosmetics. In one application, the keratin powder is admixed with other cosmetic ingredients. The keratin power, when brought into contact with water from the other cosmetic ingredients or from the skin of the wearer, forms a hydrogel which forms a protective layer over the skin and also retains moisture against the skin. The keratin powder, which has beneficial properties for skin, is thus held against the skin, moisturizing the skin. In some embodiments, the keratin powder includes soluble peptides which can diffuse out of the powder with application of water. The soluble peptides are believed to be non-antigenic, mitogenic, and have beneficial skin healing properties. Cosmetics including the hydratable keratin powder can aid in both moisturizing and healing skin. Keratin powder can also be used as an absorbent replacement to talc, the most popular cosmetic base, to which many are allergic. The keratin powder or fibrous material can be used to promote healing of damaged skin. The keratin material can be applied to skin afflictions such as diaper rash, burns, sunburns, cuts, abrasions, punctures, sores, bed sores, ulcers, diabetic ulcers, irritated skin, surgical incisions, skin graft donor sites, and wrinkled skin. In one method, the keratin material is admixed with a carrier such as a cream, lotion, or gel.

Other applications of the keratin solid include using the keratin powder or fibers in feminine hygiene products, where the keratin can serve a moisture absorbing function. Another application is found in wound exudate management. Yet another application is in anti-perspirants, where the keratin solid can absorb moisture. Still another application is in drug release applications, where the keratin can be used in powder, fiber, or film form to provide a moist, benign environment against the skin for drug release. The present invention, in powder, fiber, and non-woven sheet forms, is also believed suitable for use in forming tissue-engineering scaffolds. An additional use as a food additive is contemplated, as some naturally-derived products, such as gelatin, are already used in food products.

The keratin can also be used as the precursor to the formation of a gel, which can form a keratin hydrogel upon the addition of water to the absorbent keratin solid. The keratin can be used to form an in situ gel. In the in situ application, the keratin powder can reside within an envelope predisposed at a site and the water added into the envelop already in position. The keratin can be stored in solid form, for example as a fiber, powder, or some combination thereof, and water added later. Keeping the keratin in solid form allows for storage and later gel formation only when desired, as in an emergency medical field dressing application. Requiring the keratin to pass through a solid step also serves to purify the resulting gel, as many impurities are removed in the intermediate processing steps.

The present invention can also be used to augment soft tissue. Keratin hydrogel precursor in powder form may be suspended in an injectable carrier and injected subdermally. In one method, the keratin powder is suspended in saline and injected subdermally.

The resulting hydrogel has been observed to have viscoelastic properties, favorable for use as an implant filler such as a breast implant. The hydrogel has been observed to flow more readily when manipulated, which may prove beneficial to implant applications where the consistency of the implant is important.

The present invention can be used in a wound dressing including the water absorbent keratin fiber formed into a non-woven dressing. The keratin fibers can be formed into a non-woven fiber using methods similar to those conventionally used to form fibers into non-woven sheets well known to those skilled in the art. Upon the addition of water, the keratin fibers can form a hydrogel and leach peptides into the wound.

Numerous advantages of the invention covered by this document have been set forth in the foregoing description. It will be understood, however, that this disclosure is, in many respects, only illustrative. Changes may be made in details, particularly in matters of reagents, concentrations, and step order, without exceeding the scope of the invention. The invention's scope is, of course, defined in the language in which the appended claims are expressed.

What is claimed is:

1. A process for making a hydratable keratin solid comprising:

oxidizing insoluble keratin in a first solution comprising a soluble oxidizing agent, such that a portion of the disulfide bonds of said insoluble keratin are oxidized to form sulfonic acid residues, to obtain an oxidized insoluble solid fraction;

separating said oxidized insoluble solid fraction from said first solution;

contacting said oxidized insoluble solid fraction with a second solution comprising monovalent cations dissolved in a solvent;

maintaining said second solution containing said oxidized insoluble solid fraction and said monovalent cations for a time and at a temperature effective to cause an interaction between said sulfonic acid residues and said monovalent cations to obtain a salt suspension of said insoluble keratin and said monovalent cations; and substantially removing the solvent from said salt suspension to obtain a hydratable insoluble keratin solid.

2. A process of claim 1 further comprising adjusting the pH of said second solution, to obtain a substantially neutral solution.

3. A process as recited in claim 1, wherein said keratin is obtained from mammal hair, fur, skin, horns, hooves, or bird feet, beaks or feathers.

4. A process as recited in claim 1, wherein said keratin is obtained from human hair.

5. A process as recited in claim 1, wherein said oxidizing agent is hydrogen peroxide, peracetic acid, perborates, percarbonates, benzoyl peroxide, or ammonium sulfate peroxide.

6. A process as recited in claim 1, wherein said oxidizing agent is at a concentration of between about 1 and about 35 weight/volume percent.

7. A process as recited in claim 1, wherein said oxidizing agent is at a concentration of from about 1 to about 20 weight/volume percent.

8. A process as recited in claim 1, wherein said oxidizing agent is at a concentration of from about 2 to about 4 weight/volume percent.

9. A process as recited in claim 1, wherein said oxidizing agent is at a concentration of from about 10 to about 15 weight/volume percent.

10. A process as recited in claim 1, wherein said keratin is oxidized at a temperature between about 0° C. and about 100° C.

11. A process as recited in claim 1, wherein keratin is oxidized at a temperature between about 20° C. and about 100° C.

12. A process as recited in claim 1, wherein said keratin is oxidized at a temperature between about 80° C. and about 100° C.

13. A process as recited in claim 1, wherein said keratin is oxidized for a period of between 0.5 and about 24 hours.

14. A process as recited in claim 1, wherein said keratin is oxidized for a period of between about 1 and about 4 hours.

15. A process as recited in claim 1, wherein the keratin is oxidized by suspending said keratin in a solution of between about 1 percent and about 32 percent peracetic acid at a temperature between about 0° C. and about 100° C. for between about 0.5 and about 24 hours.

16. A process as recited in claim 1, wherein the keratin is oxidized by suspending said keratin in a solution of about 4 percent peracetic acid at a temperature of about 4° C. for about 24 hours.

17. A process as recited in claim 1, wherein the keratin is oxidized by suspending said keratin in a solution of about 4 percent peracetic acid at a temperature between about 20° C. and about 100° C. for between about 1 and about 4 hours.

18. A process as recited in claim 1, wherein said second solution containing the oxidized solid fraction and the monovalent cations is boiled for between about 0.5 hours and about 12 hours.

19. A process as recited in claim 1, wherein said oxidized keratin and said monovalent cations are allowed to react at a temperature of between about 15° C. and about 30° C. for a period of between about 1 and about 24 hours.

20. A process as recited in claim 1, wherein said oxidized keratin and said monovalent cations are allowed to react at a temperature of between about 20° C. and about 25° C. for a period of between about 1 and about 5 hours.

21. A process as recited in claim 1, wherein said basic solution comprising monovalent cations dissolved in a solvent comprises a solvent selected from methanol, ethanol, propanol, ether, tetrahydrofuran, acetone, dioxane, or glycol.

22. A process as recited in claim 1, wherein the second solution solvent is substantially removed by drying said solution under vacuum to obtain a hydratable keratin solid.

23. A process as recited in claim 1, wherein said interaction comprises the formation of ionic bonds.

24. A process as recited in claim 1, further comprising shredding said hydratable keratin solid into fibers.

25. A process as recited in claim 1, further comprising grinding said hydratable keratin solid into powder.

26. A process for making a keratin hydrogel comprising adding water to a hydratable keratin solid of claim 1.

27. A process for making a keratin viscoelastic hydrogel comprising adding water to a hydratable keratin solid of claim 1.

28. A process for making a keratin hydrogel comprising:
 oxidizing keratin in a first solution comprising a soluble oxidizing agent, such that at least some of the disulfide bonds of said keratin are oxidized to form sulfonic acid residues, to obtain an oxidized solid fraction;
 separating said oxidized solid fraction from said first solution;
 contacting said oxidized solid fraction with a second solution comprising monovalent cations dissolved in a solvent;
 maintaining said second solution containing said oxidized solid fraction and said monovalent cations for a time and at a temperature effective to cause an interaction between said sulfonic acid residues and said monovalent cations to obtain a salt suspension of said keratin and said monovalent cations;
 substantially removing the solvent from said salt suspension to obtain a hydratable keratin solid; and
 adding water to said hydratable keratin solid to obtain a keratin hydrogel.

29. A process according to claim 28 further comprising adjusting the pH of said second solution, to obtain a substantially neutral solution.

30. A process according to claim 28 wherein said keratin is oxidized such that a major portion of said disulfide bonds of said keratin are oxidized to form sulfonic acid residues.

31. A process as recited in claim 28, wherein said keratin is obtained from mammal hair, fur, skin, horns, hooves, or bird feet, beaks or feathers.

32. A process as recited in claim 28, wherein said keratin is obtained from human hair.

33. A process as recited in claim 28, wherein said oxidizing agent is hydrogen peroxide, peracetic acid, perborates, percarbonates, benzoyl peroxide, or ammonium sulfate peroxide.

34. A process as recited in claim 28, wherein said oxidizing agent is at a concentration of between about 1 and about 35 weight/volume percent.

35. A process as recited in claim 28, wherein said oxidizing agent is at a concentration of from about 1 to about 20 weight/volume percent.

36. A process as recited in claim 28, wherein said oxidizing agent is at a concentration of from about 2 to about 4 weight/volume percent.

37. A process as recited in claim 28, wherein said oxidizing agent is at a concentration of from about 10 to about 15 weight/volume percent.

38. A process as recited in claim 28, wherein said keratin is oxidized at a temperature between about 0° C. and about 100° C.

39. A process as recited in claim 28, wherein keratin is oxidized at a temperature between about 20° C. and about 100° C.

40. A process as recited in claim 28, wherein said keratin is oxidized at a temperature between about 80° C. and about 100° C.

41. A process as recited in claim 28, wherein said keratin is oxidized for a period of between about 0.5 and about 24 hours.

42. A process as recited in claim 28, wherein said keratin is oxidized for a period of between about 1 and about 4 hours.

43. A process as recited in claim 28, wherein the keratin is oxidized by suspending said keratin in a solution of between about 1 percent and about 32 percent peracetic acid at a temperature between about 0° C. and about 100° C. for between about 0.5 and about 24 hours.

44. A process as recited in claim 28, wherein the keratin is oxidized by suspending said keratin in a solution of about 4 percent peracetic acid at a temperature of about 4° C. for about 24 hours.

45. A process as recited in claim 28, wherein the keratin is oxidized by suspending said keratin in a solution of about 4 percent peracetic acid at a temperature between about 20° C. and about 100° C. for between about 1 and about 4 hours.

46. A process as recited in claim 28, wherein said second solution containing the oxidized solid fraction and the monovalent cations is boiled for between about 0.5 hours and about 12 hours.

47. A process as recited in claim 28, wherein said oxidized keratin and said monovalent cations are allowed to react at a temperature of between about 15° C. and about 30° C. for a period of between about 1 and about 24 hours.

48. A process as recited in claim 28, wherein said oxidized keratin and said monovalent cations are allowed to react at a temperature of between about 20° C. and about 25° C. for a period of between about 1 and about 5 hours.

49. A process as recited in claim 28, wherein said second solution comprising monovalent cations dissolved in a solvent comprises a solvent selected from methanol, ethanol, propanol, ether, tetrahydrofuran, acetone, dioxane or glycol.

50. A process as recited in claim 28, wherein the second solution solvent is substantially removed by drying said solution under vacuum to obtain a hydratable keratin solid.

51. A process as recited in claim 28, wherein said interaction comprises the formation of ionic bonds.

52. A process as recited in claim 28, further comprising shredding said hydratable keratin solid into fibers.

53. A process as recited in claim 28, further comprising grinding said hydratable keratin solid into powder.

* * * * *